United States Patent
De Gentile (10) Patent No.: US 9,504,542 B2
(45) Date of Patent: Nov. 29, 2016

(54) TEETH CLEANING DEVICE AND METHOD (71) Applicant: Jean-Marie De Gentile, Feytiat (FR)

(72) Inventor: Jean-Marie De Gentile, Feytiat (FR)

(73) Assignees: Hugo De Gentile, Feytiat (FR), part interest; Jean-Marie De Gentile, Feytiat (FR), part interest ( * ) Notice: Subject to any disclaimer, the term of this patent is extended or adjusted under 35 U.S.C. 154(b) by 184 days.

(21) Appl. No.: 14/380,948

(22) PCT Filed: Feb. 28, 2013

(86) PCT No.: PCT/FR2013/050434
§ 371 (c)(1),
(2) Date: Aug. 26, 2014

(87) PCT Pub. No.: WO2013/128141
PCT Pub. Date: Sep. 6, 2013

(65) Prior Publication Data
US 2015/0024340 A1    Jan. 22, 2015

(30) Foreign Application Priority Data

Mar. 1, 2012   (FR) ...................................... 12 51879

(51) Int. Cl.
*A61C 17/22* (2006.01)
*A61C 17/02* (2006.01)
*A46B 9/04* (2006.01)

(52) U.S. Cl.
CPC ......... *A61C 17/228* (2013.01); *A61C 17/0211* (2013.01); *A61C 17/221* (2013.01); *A46B 9/045* (2013.01)

(58) Field of Classification Search
CPC combination set(s) only.
See application file for complete search history.

(56) References Cited

U.S. PATENT DOCUMENTS

| 3,401,690 A | * | 9/1968 | Martin | ................... A61C 17/20 433/119 |
| 3,731,675 A |   | 5/1973 | Kelly  |                                        |
| 4,560,351 A |   | 12/1985| Osborne|                                        |
| 5,104,315 A | * | 4/1992 | McKinley | .......... A61C 17/0211 433/216     |

(Continued)

FOREIGN PATENT DOCUMENTS

| DE | 10153245 | 5/2003 |
| DE | 10230736 | 1/2004 |

(Continued)

OTHER PUBLICATIONS

International Search Report dated Jun. 19, 2013, corresponding to PCT/FR2013/050434.

*Primary Examiner* — David Walczak
(74) *Attorney, Agent, or Firm* — Young & Thompson (57) ABSTRACT A device for cleaning teeth, allows the simultaneous cleaning of the teeth of at least one arch. The device includes: a single or a double arc-shaped tray which can enclose the teeth of one arch or both arches at once and which, via the free edge(s) thereof, can be fitted to the corresponding gum or gums, the tray made from a flexible material allows reversible deformation and is compatible with medical use; and fluid-injection/-removal elements for injecting fluid into the tray and removing fluid from the interior thereof. Once the tray is in place on the teeth, the fluid-injection/-removal elements subject them to repeated cycles of fluid injection/removal to clean the teeth by the combined action, within the tray, of fluid circulation over and between the teeth and mechanical action of the tray's internal surface on the teeth, resulting from the deformation of the tray during the injection/removal cycles.

16 Claims, 5 Drawing Sheets

(56) References Cited

U.S. PATENT DOCUMENTS

| | | | |
|---|---|---|---|
| 5,443,386 A * | 8/1995 | Viskup | A61C 17/0211 433/216 |
| 7,537,451 B1 | 5/2009 | Ramnarine | |
| 2010/0151407 A1 | 6/2010 | Rizoiu | |
| 2011/0027746 A1 | 2/2011 | McDonough et al. | |

FOREIGN PATENT DOCUMENTS

| | | |
|---|---|---|
| EP | 1506746 | 2/2005 |
| WO | 200594719 | 10/2005 |
| WO | 2010024798 | 6/2011 |

* cited by examiner

TEETH CLEANING DEVICE AND METHOD

BACKGROUND OF THE INVENTION

Field of the Invention

The present invention relates to a teeth cleaning device and method for simultaneously brushing all the teeth of at least one arch.

Description of the Related Art

Its very simple use protocol is particularly intended for people with reduced mobility and, more generally, for all those having difficulties to clean their teeth with the traditional brushing systems.

Teeth cleaning is conventionally performed using a toothbrush. To be efficient, its handling requires learning and skill which are sometimes lacking.

The automation of the movements of the head of the electrical toothbrush facilitates its use but equally requires a good coordination and the compliance with a strict protocol. Cleaning is optimal only when it concerns a "standard" dental arch, namely without crooked teeth, and when the periodontal tissues are healthy. This ideal situation is rarely met with persons with disabilities.

It is then necessary to resort to systems adapted to complement and perfect the dental hygiene: the water toothpick, the floss and the interdental brush, the disinfecting mouthwashes. Their use is restricted to sufficiently skilled subjects and requires long minutes of patience.

There also exist particular situations, such as those of militaries on the move or in operation, for which ensuring the oral hygiene is difficult using a toothbrush.

The present inventor sought a solution overcoming all these disadvantages and, to this end, developed a teeth cleaning device according to which cleaning is performed by a contraction (which can also be referred to as being a constriction) and a relaxation, according to successive cycles, of a shell or gutter/mouth piece made of a resilient material receiving and enclosing all the teeth of an arch or of both arches.

To the best knowledge of the applicant, no document of the prior art which describes a teeth cleaning or a dental treatment using a mouth piece or the like, such as US 2010/0151407 A1, EP 1506746, WO 2005/94719 A1, U.S. Pat. No. 7,537,451 B1, DE 10153245, WO 2010/02498 A1, has suggested to perform a teeth cleaning by successive relaxation and contraction movements of a flexible mouth piece around the teeth of an arch or of two arches to be cleaned, said mouth piece being advantageously internally covered with a coating adapted to perfect the removal of soiling and of the dental plaque from the teeth and the interdental spaces, and the relaxation-contraction cycles being advantageously caused by the alternatively performed repeated operations of injecting in the mouth piece a fluid, namely a disinfecting new fluid, and then of evacuating from said mouth piece said used disinfecting fluid.

Thus, in the case of using such a disinfecting fluid, the present invention provides the complementary advantage of allowing to perform as efficiently the cleaning and the disinfection of the teeth and of the interdental spaces, regardless of the configuration of the arches.

Furthermore, according to a particularly interesting embodiment, the use, for ensuring such relaxation-contraction cycles, of a device exerting pressure/depression cycles (pressure/depression cycle generator) within the mouth piece allows to automate all the cleaning operations and requires no complex handling.

Thus, the invention allows to reduce the time dedicated to the oral hygiene and to the brushing to a few seconds and significantly increases its efficiency.

SUMMARY OF THE INVENTION

The present invention thus firstly relates to a teeth cleaning device for simultaneously cleaning the teeth of at least one arch, characterized by the fact that it comprises a single or double arc-shaped mouth piece, adapted to enclose the teeth of an arch or of both arches at the same time, respectively, and to adapt, by its free edge or edges, on the corresponding gum or gums, said mouth piece being made of a flexible material accepting a reversible deformation and compatible with a medical use, and fluid injection/extraction means for injecting fluid in the mouth piece and extracting said fluid from the inside of the mouth piece, said fluid injection/extraction means subjecting the mouth piece, once the latter is fitted on the teeth for their cleaning, to repeated fluid injection/extraction cycles causing pressurization/depressurization cycles of the mouth piece for cleaning the teeth by a combined action, in the mouth piece, of a fluid circulation on the teeth and between the teeth and a mechanical action of the internal surface of the mouth piece on the teeth, resulting from the relaxation and the constriction of the mouth piece during the injection and extraction cycles, respectively.

The overall shape of a simple mouth piece at rest is advantageously such that it can, for a given user, indifferently enclose the teeth of the upper maxilla or those of the lower maxilla (mandible). Indeed, the size correspondence of the upper and lower arches linked by the dental occlusion is such that, for the vast majority of people, a one and only mouth piece, given its elasticity, can adapt to both maxillae.

A simple mouth piece thus has the complementary shape of a recess of a dental arch to which it conforms by extending largely over the gum on both sides of the teeth.

On a front section passing through a median sector of the jaws, the contour of a simple mouth piece laterally begins at the bottom of the gingival-jugal sulcus and then bypasses the tooth leaving a gap corresponding to the thickness of an internal coating or to the height of the bristles internally covering the mouth piece when such a coating or bristles are provided such as described thereafter, and ends, in the case of the upper maxilla, in contact with the palatal mucosa and, in the case of the mandible, in the gingival-lingual mucous reflection area.

Indeed, the mouth piece can advantageously have, on at least one part of its internal surface, a non-smooth surface state or a non-smooth coating or interface, allowing it to promote the deconstruction of the dental plaque.

Thus, the mouth piece can have an internal surface, partially or entirely covered with reliefs, especially bristles in the manner of a brush. In particular, it can be provided that the internal surface of the mouth piece is covered with bristles on the whole surface facing the teeth.

The bristles can be of any kind and are intended, during the contraction/relaxation movements of the mouth piece, to deconstruct the dental plaque by friction and crushing.

Further technical solutions can be contemplated to obtain the same result of deconstruction of the dental plaque. It is thus possible to provide that a mouth piece has a slightly abrasive, porous, of the foam or sponge-type, flexible (which can be said to be depressible) interface having mechanical properties compatible with the teeth cleaning, the interface being interposed between the mouth piece and the teeth.

What has just been indicated for a simple mouth piece also applies for each mouth piece of a double mouth piece.

A mouth piece according to the invention is advantageously made in a flexible material which can be selected from flexible materials impermeable to gases (such as air) and liquids (water, cleaning liquid, disinfecting liquid), such as latex or silicone compatible with a medical use.

The technical advances made in the field of silicone for food use make this type of material the ideal constituent of the mouth piece.

The thickness of the mouth piece depends on the flexibility of the material used. It must maintain its shape without collapsing on itself. A final relative rigidity is required for facilitating its manipulation. The softer the consistency of the silicone will be, the thicker it must be.

The silicone nursing bottle nipples are an example of an ideal compromise between rigidity and flexibility, ensuring an optimal hold of the shape while preserving the resilient properties.

As in the case of a nursing bottle nipple, a non-homogeneous distribution of the resilient material, defining more or less thick areas, could serve as an armature.

Since the mouth piece is intended to undergo a depression for pressing it against the teeth as will be described thereafter, it should be advantageously provided on its entire free edge with a peripheral seal adapted to hold under the best possible conditions the air leaks resulting from the suction.

In other words, the mouth piece preferably sealingly or substantially sealingly fits by its free edge or edges on the corresponding gum or gums.

By "substantially sealingly" is meant that a small amount of fluid (air, liquid, saliva) can be allowed to enter the mouth piece positioned on the gum or gums provided that the repeated contraction/relaxation of the mouth piece can be correctly performed. However, it has been noted that, in operation, the cheeks and the lips, by abutting against the mouth piece, perfect the seal thereof on the gum or gums.

The peripheral adaptation of the mouth piece on the gum can be obtained by several technical solutions such as a "bellows" edge or a thicker edge made of a silicone with a lower hardness. Since the reason for this differential edge is to obtain the best possible pressing regardless of the anatomic configuration of the dental arches and their mucous environment, it must be designed sufficiently deformable and plastic for tightly conforming to the reliefs of the inside of the mouth. Moreover, since it has a lower hardness, it can avoid damaging the gums.

Thus, the free edge or edges of the mouth piece, simple or double respectively, can particularly be thickened in the shape of bulge. As indicated, this bulge can have a lower hardness than the rest of the mouth piece.

In the case of a device comprising a double mouth piece, said double mouth piece can be constituted by two simple mouth pieces attached by their bottom with or without communication opening(s) therebetween.

In other words, the mouth piece can be designed so as to simultaneously enclose both upper and lower dental arches. In this case, the two mouth pieces constituting this double mouth piece are secured to each other. This junction can be either a sealed junction, in which case both mouth pieces do not communicate with each other and there is no fluid exchange from one to the other, or a permeable junction, by the presence of the above-mentioned opening or openings, such that there is a transmission from one to the other of the fluids as well as of the pressure-depression cycles of a pressure-depression generator, as will be described in what follows.

In the first case, since each mouth piece composing the double mouth piece is independent from the other, the transmission of the pressures and the depressions will be via two independent pairs of transmission conduits, one of the conduits for injecting a fluid in the mouth piece and the other for extracting it.

In the second case, only one pair of transmission conduits will allow this injection and this extraction. These transmission conduits are described in more detail thereafter.

A mouth piece according to the invention can be manufactured by molding of a flexible material (such as silicone), with the reliefs (bristles) integrally molded with the mouth piece or integrated during the molding setting in the form of a fabric or a web having, for example, Nylon bristles.

In the case of a bulge provided on the edge of the mouth piece having a lower hardness than the rest of the mouth piece, this bulge could be formed by being separately injected in the mold or separately molded and then bonded to the rest of the mouth piece during the final setting, both portions being sticky at that time.

Furthermore, a mouth piece according to the invention can advantageously carry a gripping member for constituting a handle facilitating its insertion in the mouth.

Indeed, it is possible to add to a mouth piece according to the invention a handle-shaped gripping system so that it can be more easily inserted in the mouth and held, during its operation, pressed against the mucous membranes, thereby promoting the peripheral hermeticity. The mouth piece is then advantageously supported by a rigid structure extended in its anterior portion by a handle.

The mouth piece can also be inserted in a rigid receptacle adapted to be inserted in the mouth, wherein said receptacle can comprise a gripping member for constituting a handle facilitating its insertion in the mouth.

The device according to the invention can also comprise a bite or occlusion plane located opposite the triturating portion of the antagonistic teeth for maintaining it in the mouth by closing the jaws, said bite or occlusion plane being carried by the mouth piece or by a gripping member carried by the mouth piece or by a rigid receptacle in which the mouth piece is inserted.

The subjects which are able to do it can, with such a bite or occlusion plane, maintain their mouth piece by tightening the jaws thereon.

According to a first embodiment of the present invention, the fluid injection/extraction means comprise at least one port made in said mouth piece for suctioning, by the wearer himself or herself, air and/or saliva it contains in order to contract the mouth piece, and then when the wearer stops suctioning, returning the air and/or saliva into said mouth piece for relaxing it.

The mouth piece can comprise at least one port for injecting/extracting fluid therein/therefrom.

In this case, the purging of the food residues is performed, similarly to a conventional brushing, by rinsing the mouth and the resilient mouth piece. This first embodiment corresponds to a particular use which, while remaining incidental, allows to improve the oral hygiene condition of persons on the move such as military.

According to a second embodiment of the present invention, which is particularly preferred because it can impart to the device according to the invention its maximum efficiency with a short tooth brushing time, the fluid injection/extraction means inject in the mouth piece, in an injection phase, a dose of at least one fluid selected from air, an inert gas and a liquid, particularly a cleaning and/or disinfecting liquid, and extract, in an extraction phase, said fluid dose from said mouth piece.

In particular, the fluid injection/extraction means can comprise a first fluid circuit connecting a new fluid reservoir to the inside of the mouth piece, a second fluid circuit connecting the inside of the mouth piece to a used fluid reservoir, pump means for circulating new fluid Fn in the first new fluid circuit to the mouth piece and for circulating used fluid in the second fluid circuit from the mouth piece to the used fluid reservoir, and valve means for isolating both fluid circuits from each other such that the flow of new fluid Fn is isolated from that of the used fluid Fu.

According to particular features:
- the first fluid circuit comprises, in order from the new fluid reservoir to the mouth piece, a first one-way valve, a branch to the chamber of a first plunger and a second one-way valve;
- the second fluid circuit comprises, in order from the mouth piece to the used fluid reservoir, a third one-way valve, a branch to the chamber of a second plunger and a fourth one-way valve;
- said first and second plungers have synchronous suction and discharge movements;
- the chambers of the first and second plungers are adapted to contain a same fluid dose;
- the second and fourth one-way valves are closed by a suction movement of the first and second plungers, respectively, and opened by a discharge movement of the first and second plungers, respectively;
- the first and third one-way valves are closed by a discharge movement of the first and second plungers, respectively, and opened by a suction movement of the first and second plungers, respectively;

whereby, during a suction movement of the first and second plungers, new fluid Fn is suctioned from the new fluid reservoir into the chamber of the first plunger, the used fluid Fu in the mouth piece being meanwhile passed into the chamber of the second plunger, the used fluid Fu of the mouth piece being prevented from penetrating the first fluid circuit by closing the second one-way valve and the used fluid Fu being prevented from circulating toward the used fluid reservoir by closing the fourth one-way valve and, during a discharge movement of the first and second plungers, new fluid is ejected from the chamber of the first plunger toward the mouth piece and used fluid Fu is ejected from the chamber of the second plunger toward the used fluid reservoir, the new fluid Fn being prevented from circulating in the second fluid circuit by closing the third one-way valve and the new fluid Fn being prevented from returning toward the new fluid reservoir by closing the first one-way valve, this arrangement allowing, during the fluid injection/extraction cycles, to avoid any mixing of the new fluid Fn and the used fluid Fu.

Means for controlling the plungers can be constituted by an electrical motor, the rotational movement of which is converted into a translation movement of said plungers by a mechanical device, wherein a rheostat for controlling the frequency of the pressurization and depressurization cycles of the mouth piece and/or a timer setting the operating time of the motor can be associated to said motor.

According to a particular alternative embodiment, the first fluid circuit further comprises, between the second one-way valve and the mouth piece, a first fitting, the second fluid circuit further comprises, between the mouth piece and the third one-way valve, a second fitting, said first and second fittings allowing to connect/disconnect the first and second fluid circuits to/from the mouth piece, the first and second fittings being further adapted to cooperate with corresponding fittings of a pouch for inserting, the mouth piece being disconnected from the first and second fluid circuits, said pouch between the first and second fluid circuits for cleaning said first and second fluid circuits by purging.

Both fluid circuits can open into the mouth piece near each other, advantageously in the front central portion of said mouth piece.

The present invention also relates to a method for simultaneously cleaning the teeth of at least one arch, characterized by the fact that the mouth piece, which is simple or double, of a device as above-defined is adapted on one or both of the dental arches, respectively, and that repeated cycles for contracting the mouth piece on the teeth and relaxing this contraction are performed until the teeth and interdental spaces are cleaned by suctioning a fluid volume in said mouth piece and returning therein an equivalent fluid volume, respectively.

According to an optional particular feature of the method according to the present invention, 20 to 40 contraction and relaxation repeated cycles are performed during a period of time of 10 to 20 seconds.

Thus, according to a particularly preferred embodiment for cleaning teeth according to the invention:
- in a first step, a cleaning liquid is injected via a plunger within the mouth piece made of a flexible and resilient material similar to a mouth protector, enclosing the dental arch. This has the effect of discreetly increasing the pressure within this resilient mouth piece and evenly distributing the fluid injected around the teeth and in the interdental spaces; and
- in a second step, this cleaning fluid is evacuated by suction, following a circuit separate from the injection circuit, and this short depression contracts the resilient mouth piece by pressing against the teeth the bristles internally covering it. The mechanical action of the bristles on the teeth removes the dental plaque. The repetition of the injection and ejection cycles ensures the discharge of the plaque and the cleaning of the teeth.

BRIEF DESCRIPTION OF THE DRAWING FIGURES

To better illustrate the subject-matter of the present invention, several embodiments will be described thereafter, for indicative and non-limiting purposes, with reference to the appended drawings.

On the drawings.

DETAILED DESCRIPTION OF THE INVENTION

Figure 1:
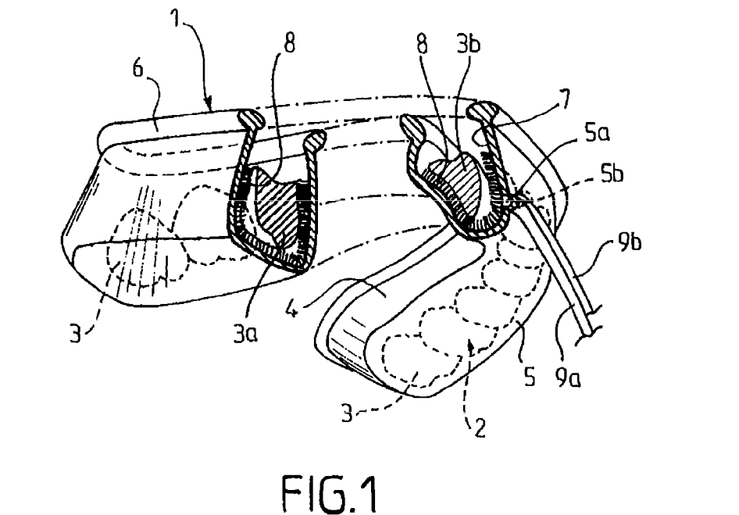
FIG. 1 is a perspective view with a partial cutaway of a device for cleaning the teeth of an upper arch according to a first embodiment of the present invention.

With reference to FIG. 1, it can be seen that a simple shell or mouth piece 1 has been represented, closed at its ends, having the shape of an arc corresponding to a dental arch 2, the mouth piece 1 being shown fitted in place around this arch 2, that is, in the position in which it encloses the teeth 3 of this arch 2.

The mouth piece 1 has a generally U-shaped section having two side walls 4 joined at their opposed ends and connected to a bottom 5. Both side walls 4 become slightly closer to each other in the vicinity of their free edges, where they form a bulge 6 extending on the entire periphery of the mouth piece 1. The bulge 6 has a roughly cylindrical section.

In the illustrated example, the mouth piece 1 is made of silicone, from a mold allowing to obtain a silicone thickness of about 2 mm, with an average hardness number (Shore 30), conforming to the shape of a dental arch; the thicker bulge 6 corresponds to a cylinder with a diameter of about 4 mm and is made with a silicone with a lower hardness number (Shore 10).

As indicated, the narrowed walls of the mouth piece 1 along its free edge allow to exert on the mucous membrane a retention pressure.

The internal surface 7 of the mouth piece 1, that is, its internal surface in contact with the teeth 3, is covered with bristles 8, the base of which is integrated in the silicone wall. They are distributed as the bristles of a toothbrush would be but are less long and more flexible. Indeed, the space dedicated thereto being small (1 to 3 mm in the example shown), their length is selected for ensuring the cleaning of the gingival and dental tissues without damaging them. They are advantageously made of an end-rounded Nylon thread, again not to damage the gingival and dental tissues.

On the left and right parts of FIG. 1 can be seen more precisely the position of the mouth piece 1 with respect to the arch at a cut passing through the second premolar 3a and at a cut passing through the right central incisor 3b, respectively.

The mouth piece 1, once in place on the arch 2, is adapted to receive a new fluid Fn for sweeping away the detritus removed from the teeth 3 during cleaning, the used fluid Fu must then be evacuated (see FIGS. 11 and 12 which will be described in more detail thereafter).

The injection and the extraction of this cleaning fluid in and out of the mouth piece 1 is via two ports 5a, 5b made in the front portion thereof, just facing the free edge of the incisors. These two ports 5a, 5b constitute the areas for connecting two transmission conduits 9a, 9b, respectively, external to the mouth piece 1, having a length of a few centimeters, which end by a fitting (not shown) of a system for connecting two corresponding conduits 10a, 10b from the pressure-depression generator 11, as will be described thereafter with reference to FIG. 13.

These transmission conduits 9a, 9b could be positioned indifferently at any points of this surface. However, for accessibility and comfort reasons, it is sensible to position them in the front part of the mouth piece 1, facing the central incisors, as indicated in FIG. 1.

Figure 2:
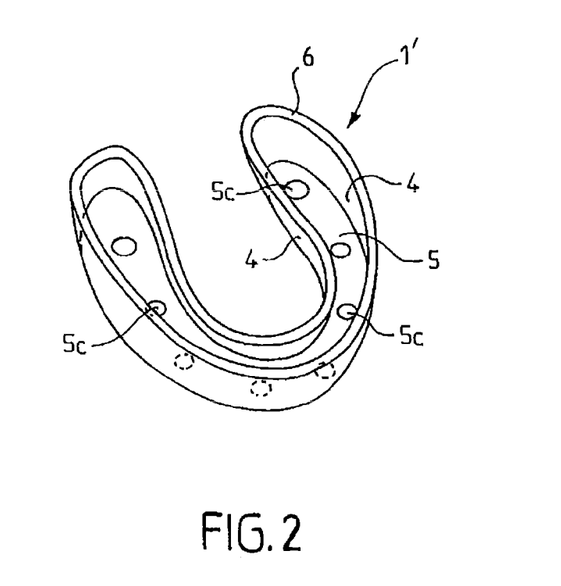
FIG. 2 is a perspective view of a device for cleaning the teeth of an arch according to a second embodiment of the present invention.

In FIG. 2, a mouth piece 1', similar to the mouth piece 1, is represented, but not covered with bristles, not comprising ports to which the transmission conduits 9a, 9b connect with a pressure-depression generator 11, and comprising ports 5c made in its bottom 5.

The mouth piece 1' constitutes an independent and autonomous mouth piece which can ensure a cleaning of the teeth following the principle of the invention of contraction/relaxation on the teeth to be cleaned under the action of the movements of the mouth of the user himself or herself, the air and/or saliva passing through the ports 5c. This embodiment represents a particular case being useful in some circumstances as mentioned above.

Figure 3:
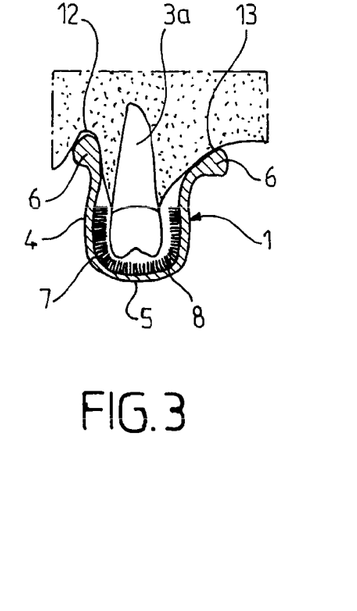
FIGS. 3 and 4 are sectional schematic views of the mouth piece of FIG. 1 fitted on the upper arch, at a premolar, in the respective relaxation and contraction positions.
Figure 4:
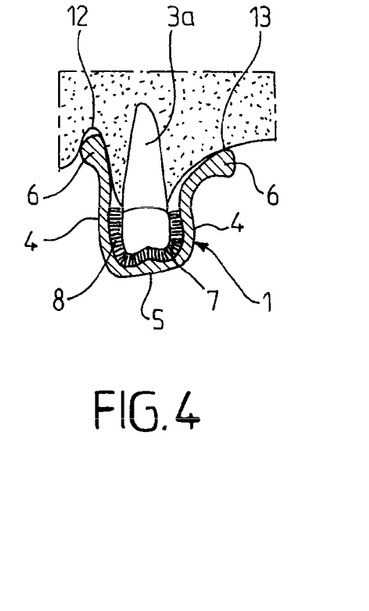

FIGS. 3 and 4 repeat, in more detail, the sections of the mouth piece 1 passing through the premolar 3a in the respective relaxation and contraction positions, the bristles 8 narrowing on the tooth in the contraction position. In the drawing, the mouth piece 1 has been represented with the ends of the bristles not pressing against the teeth in the relaxation position of FIG. 3. In reality, the bristles 8 could already be pressing against the teeth in this position.

In FIGS. 3 and 4, it can be noted that the peripheral bulge 6 has adapted to the gingival-jugal sulcus 12 as well as to the palate 13.

Figure 5:
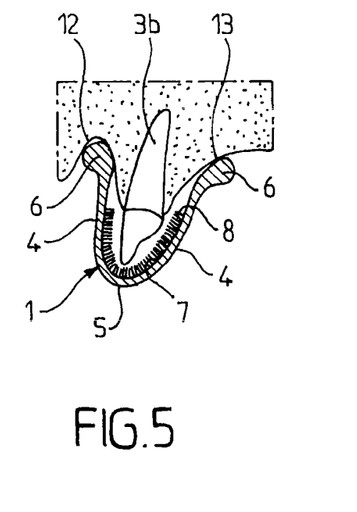
FIGS. 5 and 6 are sectional schematic views of the mouth piece of FIG. 1 fitted on the upper arch, at a central incisor, in the respective relaxation and contraction positions.
Figure 6:
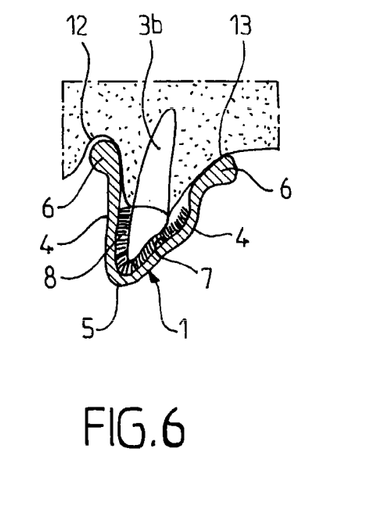

FIGS. 5 and 6 are similar to FIGS. 3 and 4, respectively, showing the mouth piece 1 at a central incisor 3b.

Figure 7:
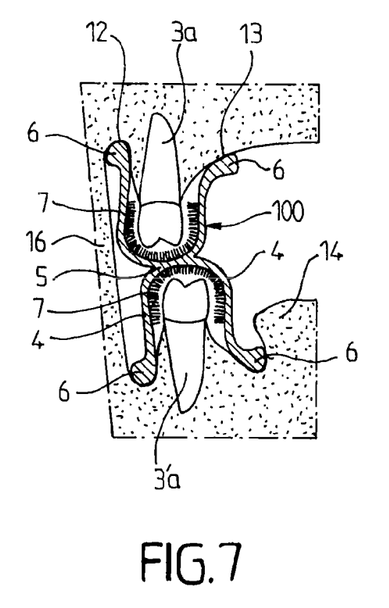
FIGS. 7 and 8 are sectional schematic views of a double mouth piece fitted on the upper and lower arches, at the premolars and central incisors, respectively, in the relaxation position.
Figure 8:
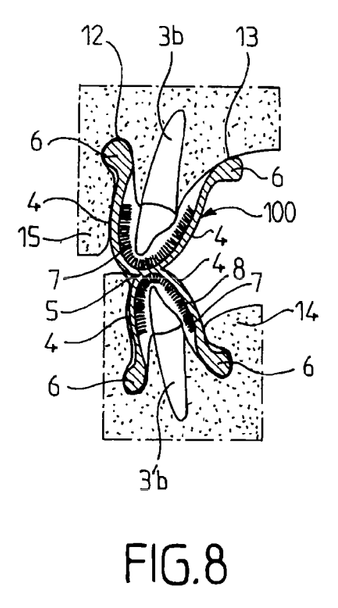

With reference to FIGS. 7 and 8, in which the tongue 14, the upper lip 15 and the cheek 16 have been shown, it can be seen that views similar to FIGS. 3 and 5, respectively, of a double mouth piece 100 adapted to enclose both the upper arch and the lower arch of a dentition are shown. The double mouth piece 100 is constituted by two mouth pieces similar to the mouth piece 1, the openings of which are oriented in opposite directions and which are attached by their bottoms 5.

As previously indicated, conduits such as the conduits 9a, 9b will be associated to each mouth piece of this double mouth piece 100.

Figure 9:
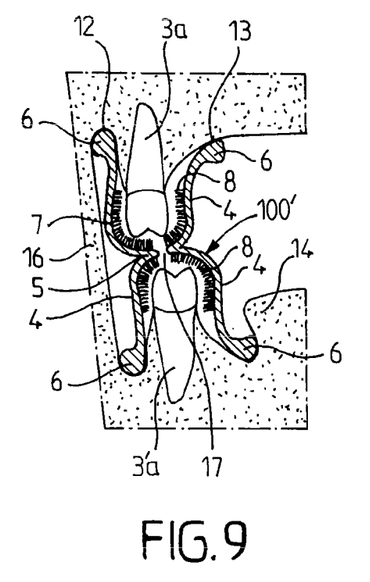
FIGS. 9 and 10 are views similar to FIGS. 7 and 8, respectively, of an alternative of the double mouth piece.
Figure 10:
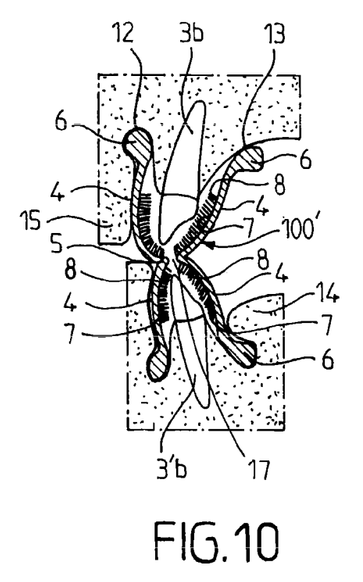

With reference to FIGS. 9 and 10, it can be seen that views similar to FIGS. 7 and 8, respectively, are shown showing a double mouth piece 100' made according to an alternative embodiment of the mouth piece 100 of FIGS. 7 and 8, alternative embodiment according to which the common bottom 5 has at least one port 17, the port or ports 17 being adapted to transmit the pressure differences from one mouth piece to the other of the double mouth piece 100'.

Thus, the double mouth piece 100' comprises a single conduit 9a and a single conduit 9b.

Figure 11:
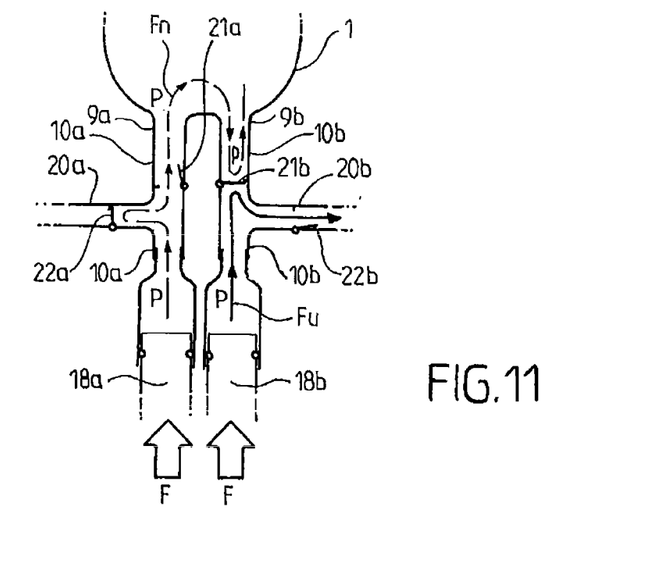
FIGS. 11 and 12 are diagrams illustrating the new fluid and used fluid paths toward and from the mouth piece of the device of FIG. 1, respectively, causing the relaxation of said mouth piece with respect to its contact with the teeth, and the contraction of said mouth piece, which surrounds the teeth, respectively.
Figure 12:
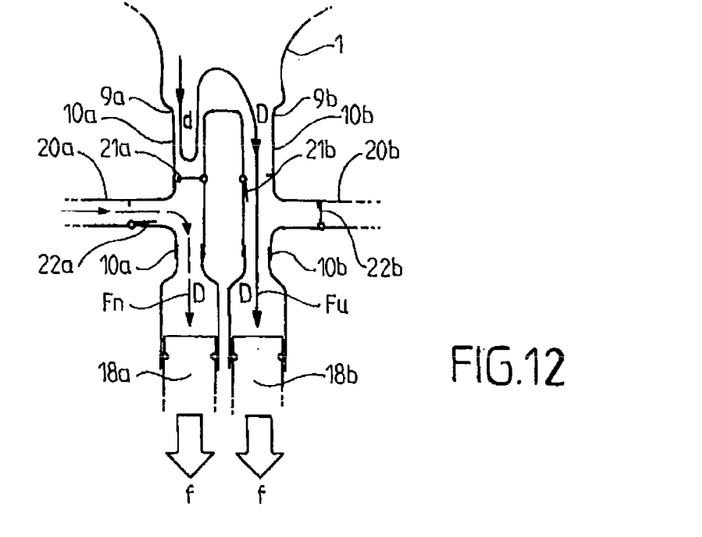

With reference to FIGS. 11 and 12, it can be seen that the circulation of a new fluid Fn injected into a mouth piece 1 is schematically shown, for causing the relaxation of its wall, thereby disengaging it from the teeth, and that of a used fluid Fu, the extraction of which by depression out of the mouth piece 1 causes the contraction thereof against the teeth. By repeated and very fast relaxation-contraction cycles, a perfect cleaning of the teeth is obtained according to the invention, with a very short time, as will be described thereafter.

To this end, plungers 18a, 18b move in a chamber 19a, 19b (FIG. 13), respectively, for ejecting or suctioning volumes of the fluids Fn and Fu, respectively, which communicate with the conduits 10*a*, 10*b* (FIG. 13), respectively, connected themselves to the conduits 9*a*, 9*b* (FIG. 1), respectively.

On the path of each of the conduits 10*a*, 10*b*, is a branch 20*a*, 20*b*, respectively, the fluid Fn arriving in the conduit 10*a* by the branch 20*a*, and the used fluid Fu exiting the conduit 10*b* toward the branch 20*b*.

One-way valves 21*a*, 21*b* are arranged on the path of the conduits 10*a*, 10*b*, respectively, between the branches 20*a*, 20*b*, respectively, and the transmission conduits 9*a*, 9*b*, and one-way valves 22*a*, 22*b* are arranged on the path of the branches 20*a*, 20*b*, respectively. Small stop lines are schematically shown in FIGS. 11 and 12 at the one-way valves 21*a*, 21*b*, 22*a*, 22*b* to better illustrate the two open and closed end positions they can take and, consequently, the circulation direction of the fluids.

In FIG. 11, it can be seen that simultaneously pressing the plungers 18*a*, 18*b* along the arrows F creates a pressure P which closes the valves 21*b* and 22*a*, opens the valve 21*a* and sends in the mouth piece 1 the dose of new fluid Fn contained in the chamber of the plunger 18*a*, causing the relaxation of the mouth piece 1 with respect to its contact with the teeth, while the dose of used fluid Fu contained in the chamber of the plunger 18*b* is evacuated toward the outside of the system by the branch 20*b*, the valve 21*b* closing and the valve 22*b* opening under the pressure of the fluid Fu.

In FIG. 12, it can be seen that simultaneously withdrawing the plungers 18*a*, 18*b* along the arrows f creates a depression D which opens the valve 22*a*, closes the valve 21*a*, so as to introduce a dose of fluid Fn in the chamber of the plunger 18*a*—which dose will be ready to be ejected in the mouth piece 1 when the stroke of the plunger 18*a* reverses, and to introduce the dose of fluid Fu from the mouth piece 1 to the chamber of the plunger 18*b* by opening the valve 21*b* and closing the valve 22*b* due to the depression D from the removal of the plunger 18*b*, the dose of fluid Fu thus collected in the chamber in the plunger 18*b* being ready to be ejected toward the outside by the branch 20*b* when the stroke of the plunger 18*b* reverses.

In FIG. 11, during the discharges of the plungers 18*a*, 18*b*, the valve 21*b* is closed by abutting by the pressure P on the side of the plunger 18*b*. The mouth piece 1 is inflated by the pressure P from the conduit 10*a*, which causes a fluid circulation in the conduit 10*b* with a reduced pressure p; the pressure difference on either side of the valve 21*b* maintains it closed.

In FIG. 12, during the suctions of the plungers 18*a*, 18*b*, the valve 21*a* is closed by abutment caused by the depression D on the side of the plunger 18*a*. The mouth piece 1 is compressed by the depression D from the conduit 10*b*, which causes a fluid circulation in the conduit 10*a* with a reduced depression d; the pressure difference on either side of the valve 21*a* maintains it closed.

Figure 13:
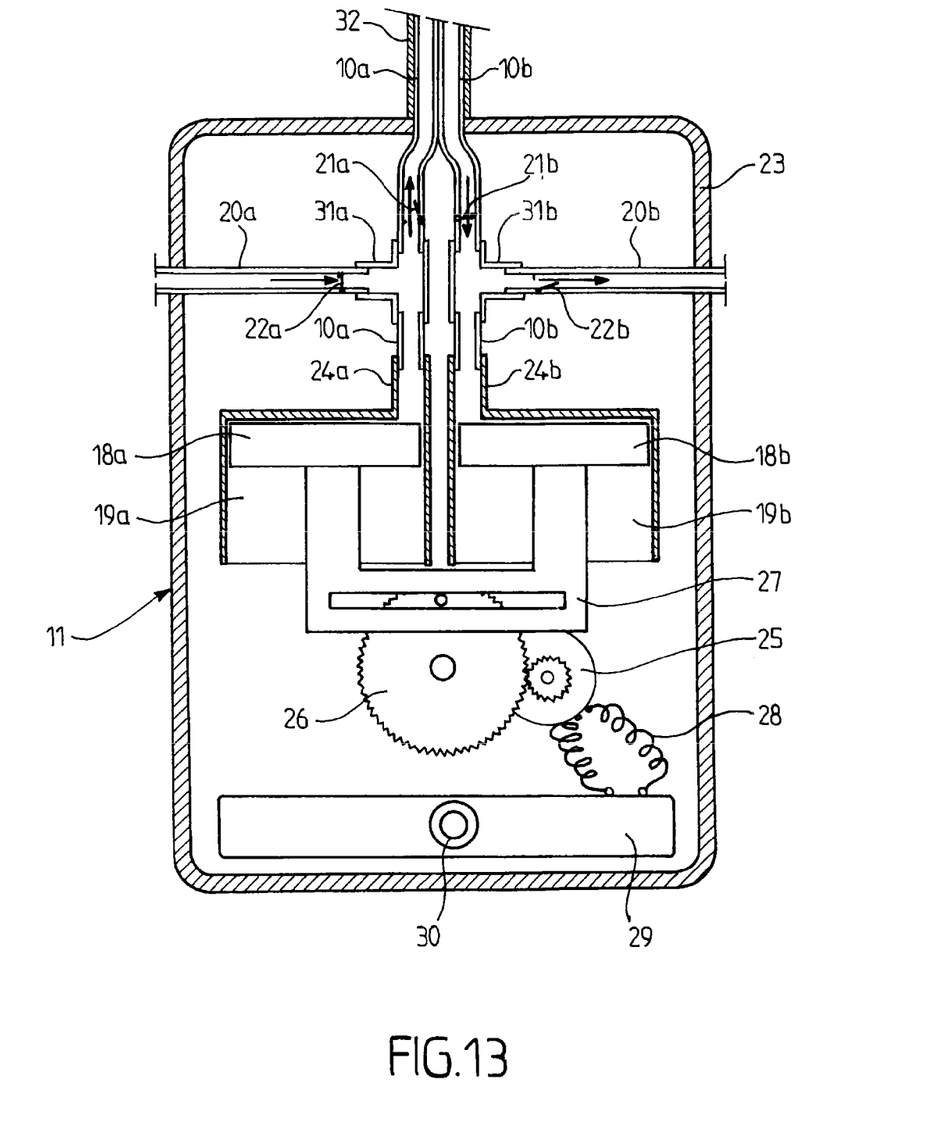
FIG. 13 is a schematic view of a pressure-depression generator ensuring a high frequency repetition of the relaxation-contraction cycles.

In FIG. 13 has been schematically shown a pressure-depression generator 11, operating according to the principle which has just been described, with reference to FIGS. 11 and 12. In this FIG. 13, it is shown in the position where the plungers 18*a*, 18*b* have completely discharged the doses of fluid Fn and Fu, respectively, that they had previously suctioned.

The same reference numerals have been taken from FIGS. 11 and 12 for designating similar parts.

In a housing 23 are mounted the plungers 18*a*, 18*b* adapted to slide in their chambers 19*a*, 19*b*. The fluid volumes moved by the plungers 18*a*, 18*b* pass in respective tubular parts 24*a*, 24*b*, constituted extensions of walls defining the chambers 19*a*, 19*b* which are sealingly connected to the base of the conduits 10*a*, 10*b*.

In the housing 23 is also mounted an electrical motor 25 adapted to drive a toothed wheel 26 which cooperates with a conventional mechanical device 27 converting the rotational movement into a repetitive translational movement for driving back and forth the plungers 18*a*, 18*b*. To this end, the device 27 is connected to the base of both plungers 18*a*, 18*b* and the electrical motor 25, powered by connecting wires 28 connected to batteries 29, transmits to both plungers 18*a*, 18*b* a back and forth reciprocating movement allowing repetitive cycles of pressing and then withdrawal.

The electronic system for controlling the motor 25 has also been designated by the reference numeral 29, the housing referred to by the reference numeral 29 comprising the batteries and the electronic system for controlling the motor 25. The control switches of the motor control electronic system are designated by the reference numeral 30.

The housing 23 also contains the injection tube of the fluid Fn (branch 20*a*), mounted on the conduit 10*a* (therefore made in two parts) by a T-fitting 31*a*, and the ejection tube of the fluid Fu (branch 20*b*) mounted on the conduit 10*b* (therefore made in two parts) by a T-fitting 31*b*.

The housing 23 also contains the four one-way valves 21*a*, 22*a*, 21*b*, 22*b*.

The sealed housing 23 envelops and secures the whole above-described device 11 and lets only the four conduits 10*a*, 10*b*, 20*a*, 20*b* protrude outside.

The conduits 10*a*, 10*b* for the mouth piece 1 are gathered into a common sheath 32. Their length, for manipulation comfort reasons, is about 1 m. They are ended by a fitting of a connecting device intended to sealingly snap in the corresponding fitting located at the end of the conduits 9*a*, 9*b* at the front of the mouth piece 1 and allowing to connect the conduits 9*a*, 10*a* and the conduits 9*b*, 10*b* during brushing of the teeth.

Indeed, this connecting system must allow without damage, without alteration, in an easy manner and repeatedly, its connection and disconnection to/from the conduits 10*a*, 10*b* connecting the mouth piece 1 to the pressure-depression generator 11 for sealingly ensuring the injection and the evacuation of the cleaning liquids.

To do so, it is possible to resort to any appropriate technical solution provided that it ensures a correct transmission of the flows ensuring alternatively the relaxation and contraction of the mouth piece; however, a "snap"-type device, such as mentioned above, remains the easiest device to implement.

The other two conduits 20*a*, 20*b*, designed to convey the fluid Fn from its storage container and to convey the fluid Fu to its evacuation container, respectively, stay independent and receive a sufficiently clear marking for avoiding any manipulation error. They are shorter than the previous ones.

One of the faces of the housing 23 comprises an impermeable control keypad allowing to turn on and off the electrical motor 25. This set of switches 30 can also control, via a rheostat, the frequency of the suction-ejection cycles and possibly set the operating time of the motor 25 using a timer.

On another one of its faces, the housing 23 comprises a trapdoor giving access to the housing of the batteries 29 allowing to replace them when they are used. The closing system of this trapdoor makes it completely waterproof.

The connecting system between the mouth piece 1 and the pressure-depression generator 11 must ensure a perfect cleanliness to all users of a personal mouth piece which would use a same generator 11. As only one generator 11 allows the operation of several mouth pieces 1, the problems generated by potential cross-contaminations must be subjected to a particular attention.

To this end, the area of the end of the double conduit 10a, 10b sheathed in 32 from the generator 11 can advantageously be provided, just before its connecting system to the ends of the conduits 9a, 9b of the mouth piece 1 with a second pair of one-way valves, adapted to open and close in the same direction as the one-way valves 21a, 21b.

For the same reason, the conduits 9a, 9b have a minimum length so as to avoid any potentially contaminated liquid backflow from the mouth piece 1 into the inside of the conduit 10a allowing to inject the cleaning fluid.

Finally, at the end of a session of use, the pressure-depression generator 11 and the array of conduits 10a, 10b, 20a, 20b must be drained using a piece allowing to connect the injection conduit 10a and the suction conduit 10b.

Thus, a piece for draining the conduit array is provided to be connected to the system instead of the mouth piece 1 at the end of use thereof. This piece is constituted by a fitting corresponding to that of the end of the conduits 10a, 10b and comprises a sealed chamber or pouch made of a resilient material, for example of a volume from 1 to 2 $cm^3$, designed to be inflated and contracted according to the circulation of the fluids. It is inserted instead of the mouth piece 1, once the use thereof is over, and allows to close the circuit for a final drainage of the device.

It is designed to stay in place for closing the circuit and allowing to store the cleaning device. In this particular embodiment, this piece is attached to the housing 23 of the generator 11.

The fittings of the system advantageously comprise a foolproof device for avoiding an inversion of the conduits.

With the mouth piece 1 and its pressure-depression generator 11, the user wishing to perform a teeth cleaning will firstly ensure that the ends of the conduits 20a, 20b for drawing and evacuating the cleaning liquid are indeed immersed in their respective containers.

The user will then insert the fittings of the conduits 9a, 9b of its mouth piece 1 to the corresponding fittings of the conduits 10a, 10b of the generator 11, respecting the direction set by the shape of the male and female parts of the fittings. Their shape is advantageously such that it allows their cooperation (co-adaptation) in only one position. A click from a flexible plastic tab inserting in its housing at the end of the stroke indicates locking is complete. It will be noted that, during deinsertion, a simple pressure on the basis of this tab will unlock the system.

After having moistened the mouth piece 1 by passing it under water, the user will insert it in his or her mouth, on one of both arches.

He or she will then control the switching on of the electrical motor 25 of the generator 11 by pushing on the trigger switch 30 located on the housing 23.

From triggering until stopping of the motor, the following operating cycles will reproduce about twice per second:

suction of the new cleaning liquid from the container toward the chamber of the first plunger 18a and, simultaneously, depression exerted in the mouth piece 1 resulting in a contraction (constriction) of the bristles around the teeth and the ejection of the fluids contained in the thus-narrowed space. Suction of these fluids into the chamber of the second plunger 18b.

injection of the new cleaning liquid from the chamber of the first plunger 18a toward the mouth piece 1 and, simultaneously, return to the normal shape thereof resulting in a distribution of this liquid around the teeth in the free space thereby created. Evacuation of the fluids contained in the chamber of the second plunger 18b toward the destination container.

The estimated number of cycles for a complete cleaning is about 30, that is, approximately 15 seconds of operation.

Once the first dental arch is cleaned, the user will insert its mouth piece on the antagonist arch for 30 new cycles.

After having removed its mouth piece, he or she can disconnect it from the pressure-depression generator 11 and briefly rinse it under water. Then, he or she will drain the circuits of the device by connecting the connecting piece instead of the mouth piece 1 and by performing several cycles unloaded. This connecting piece will remain connected until the next use of the teeth cleaning device. For practical reasons, this piece is, as already indicated, in this particular embodiment of the invention, attached to the housing of the pressure-depression generator 11 and facilitates its storage.

The mouth piece according to the invention is an independent, removable device. It is personal and individual the same as a toothbrush would be. A group of individuals can use only one pressure-depression generator and each one can connect thereto its personal mouth piece.

The mouth pieces have a limited shelf life and must be regularly replaced. Everyone can select, from a range of different sizes, the mouth piece best suited to the shape of his or her dentition. A single-use device allowing to register the shape of the dental arch will facilitate this selection.

It is of course understood that the embodiments which have been described are for indicative and non-limiting purposes, and that modifications can be made thereto without departing from the scope of the present invention.

The invention claimed is:

1. A teeth cleaning device for simultaneously cleaning the teeth of at least one arch, comprising:
    a single or double arc-shaped mouth piece, adapted to enclose the teeth of an arch or of both arches at the same time, respectively, and to adapt, by a free edge or edges of the mouth piece, on the corresponding gum or gums, the mouth piece being made of a flexible material accepting a deformation reversible and compatible with a medical use, and
    a fluid injection/extraction configured for injecting fluid in the mouth piece and extracting the fluid from an inside of the mouth piece, the fluid injection/extraction device subjecting the mouth piece, once the mouth piece is fitted on the teeth for cleaning the teeth, to repeated fluid injection/extraction cycles causing pressurization/depressurization cycles of the mouth piece for cleaning the teeth by a combined action, in the mouth piece, of a fluid circulation on the teeth and between the teeth and a mechanical action of an internal surface of the mouth piece on the teeth, resulting from the relaxation and the constriction of the mouth piece during the injection and extraction cycles, respectively.

2. The device according to claim 1, wherein at least a part of the internal surface of the mouth piece has a non-smooth surface state or a non-smooth coating or interface, allowing the internal surface to promote the deconstruction of the dental plaque.

3. The device according to claim 2, wherein the mouth piece has the internal surface, partially or entirely covered with reliefs or bristles in a manner of a toothbrush, or has a slightly abrasive spongy and porous flexible interface having mechanical properties compatible with the teeth cleaning, the interface being interposed between the mouth piece and the teeth.

4. The device according to claim 1, wherein the flexible material of the mouth piece is selected from flexible materials impermeable to gases and liquids.

5. The device according to claim 1, wherein the free edge or edges of the single or double arc-shaped mouth piece, respectively, are thickened in a shape of a bulge.

6. The device according to claim 1, comprising a double arc-shaped mouth piece, wherein the double arc-shaped mouth piece is constituted by two simple arc-shaped mouth pieces attached by a bottom with or without communication opening(s) between the two simple arc-shaped mouth pieces.

7. The device according to claim 1, wherein the device comprises a bite or occlusion plane located opposite a triturating portion of antagonist teeth for maintaining the device in the mouth by closing the jaws.

8. The device according to claim 7, wherein the fluid injection/extraction device comprises a first fluid circuit connecting a new fluid reservoir to the inside of the mouth piece, a second fluid circuit connecting the inside of the mouth piece to a used fluid reservoir, a pump configured for circulating new fluid (Fn) in the first new fluid circuit to the mouth piece and for circulating used fluid in the second fluid circuit from the mouth piece to the used fluid reservoir, and a valve configured for isolating both fluid circuits from each other such that the new fluid (Fn) circulation is isolated from the circulation of the used fluid (Fu), wherein the fluid injection/extraction device injects in the mouth piece, in an injection phase, a dose of at least one fluid selected from air, an inert gas and a liquid, in particular a cleaning and/or disinfecting liquid, and extract, in an extraction phase, said fluid dose from said mouth piece.

9. The device according to claim 8, wherein:
the first fluid circuit comprises, in order from the new fluid reservoir to the mouth piece, a first one-way valve, a branch to the chamber of a first plunger and a second one-way valve;
the second fluid circuit comprises, in order from the mouth piece to the used fluid reservoir, a third one-way valve, a branch to the chamber of a second plunger and a fourth one-way valve;
the first and second plungers have synchronous suction and discharge movements;
the chambers of the first and second plungers are adapted to contain a same fluid dose;
the second and fourth one-way valves are closed by a suction movement (f) of the first and second plungers, respectively, and opened by a discharge movement (F) of the first and second plungers, respectively;
the first and third one-way valves are closed by a discharge movement (F) of the first and second plungers, respectively, and opened by a suction movement (f) of the first and second plungers, respectively;
whereby, during a suction movement (f) of the first and second plungers, new fluid (Fn) is suctioned from the new fluid reservoir into the chamber of the first plunger, the used fluid (Fu) in the mouth piece being meanwhile passed in the chamber of the second plunger, the used fluid (Fu) of the mouth piece being prevented from penetrating the first fluid circuit by closing the second one-way valve and the used fluid (Fu) being prevented from circulating toward the used fluid reservoir by closing the fourth one-way valve and, during a discharge movement of the first and second plungers, new fluid is ejected from the chamber of the first plunger to the mouth piece and used fluid (Fu) is ejected from the chamber of the second plunger toward the used fluid reservoir, the new fluid (Fn) being prevented from circulating in the second fluid circuit by closing the third one-way valve and the new fluid (Fn) being prevented from returning to the new fluid reservoir by closing the first one-way valve, this arrangement allowing, in the fluid injection/extraction cycles, to avoid any blending of the new fluid (Fn) and the used fluid (Fu).

10. The device according to claim 9, wherein both fluid circuits lead to the mouth piece near each other, advantageously in a front central portion of said mouth piece.

11. The device according to claim 9, wherein a device configured for controlling the plungers comprises an electrical motor, a rotational movement of the electrical motor is converted into a translation movement of the plungers by a mechanical device, wherein a rheostat for controlling a frequency of pressurization and depressurization cycles of the mouth piece and/or a timer setting an operating time of the motor can be associated to the motor.

12. The device according to claim 8, wherein the first fluid circuit further comprises, between the second one-way valve and the mouth piece, a first fitting, that the second fluid circuit further comprises, between the mouth piece and the third one-way valve, a second fitting, said first and second fittings allowing to connect/disconnect the first and second fluid circuits to/from the mouth piece.

13. The device according to claim 7, wherein the fluid injection/extraction device comprises at least one port made in the mouth piece for suctioning, by the wearer, air and/or saliva contained in the mouth piece in order to contract the mouth piece, and then, when the wearer stops suctioning, returning the air and/or saliva into the mouth piece for relaxing the mouth piece.

14. The mouth piece for a device according to claim 1, wherein the mouth piece comprises at least one port for injecting fluid in the mouth piece and extracting fluid from the mouthpiece.

15. A method for simultaneously cleaning the teeth of at least one arch, wherein the single or double arc-shaped mouth piece of a device as defined claim 1 is adapted on one or both of the dental arches, respectively, and repeated cycles for contracting the mouth piece on the teeth and relaxing the contraction are performed until the teeth and interdental spaces are cleaned by suctioning a fluid volume in said mouth piece and returning therein an equivalent fluid volume, respectively.

16. The method according to claim 15, wherein 20 to 40 contraction and relaxation repeated cycles are performed during a period of time of 10 to 20 seconds.

* * * * *